United States Patent [19]

Elion

[11] Patent Number: 4,878,115
[45] Date of Patent: Oct. 31, 1989

[54] DYNAMIC CORONARY ROADMAPPING

[75] Inventor: Jonathan L. Elion, Lexington, Ky.

[73] Assignee: University of Kentucky Research Foundation, Lexington, Ky.

[21] Appl. No.: 101,074

[22] Filed: Sep. 25, 1987

[51] Int. Cl.$^4$ .............................................. H04N 5/32
[52] U.S. Cl. ...................................... 358/111; 378/95; 378/98; 378/99
[58] Field of Search ................... 358/111; 378/99, 98, 378/95; 128/654

[56] References Cited

U.S. PATENT DOCUMENTS

| | | | |
|---|---|---|---|
| 4,204,225 | 5/1980 | Mistretta | 358/111 |
| 4,204,226 | 5/1980 | Mistretta | 358/111 |
| 4,335,427 | 6/1982 | Hunt et al. | 358/111 X |
| 4,433,428 | 2/1984 | Haendle et al. | 378/99 X |
| 4,533,946 | 8/1985 | Yasuhara et al. | 378/99 X |
| 4,545,390 | 10/1985 | Leary | 128/772 |
| 4,555,728 | 11/1985 | Fenster et al. | 378/99 X |
| 4,575,752 | 3/1986 | Honda | 358/111 |
| 4,581,635 | 4/1986 | Franke | 378/99 X |
| 4,611,340 | 9/1986 | Okazaki | 358/111 X |
| 4,628,355 | 12/1986 | Ogura et al. | 378/99 X |
| 4,639,867 | 1/1987 | Suzuki et al. | 378/99 X |
| 4,641,328 | 2/1987 | Fujise | 358/111 X |
| 4,709,332 | 11/1987 | Morrison et al. | 378/99 X |
| 4,709,385 | 11/1987 | Pfeiler et al. | 378/99 |
| 4,720,843 | 1/1988 | Haaker et al. | 378/99 |
| 4,729,379 | 3/1988 | Ohe | 378/99 X |

FOREIGN PATENT DOCUMENTS 0193712 1/1986 Fed. Rep. of Germany .
123384 7/1984 Japan .

OTHER PUBLICATIONS

Tobis et al., Digital Coronary Roadmapping as an Aid for Performing Coronary Angioplasty, Am J Cardiol 1985;56:237-241.

*Primary Examiner*—Eugene R. Laroche
*Assistant Examiner*—Seung Ham
*Attorney, Agent, or Firm*—King & Schickli

[57] ABSTRACT

A dynamic coronary roadmap of the coronary artery system is produced by recording and storing a visual image of the heart creating a mask sequence, recording and storing another dynamic visual image of the heart after injection of a contrast medium thereby creating a contrast sequence, matching the different durations of two sequences and subtracting the contrast sequence from the mask sequence producing a roadmap sequence. The roadmap sequence is then replayed and added to live fluoroscopic images of the beating heart. Replay of the roadmap sequence is triggered by receipt of an ECG R-wave. The result is a dynamically moving coronary roadmap image which moves in precise synchronization with the live incoming fluoroscopic image of the beating heart.

13 Claims, 2 Drawing Sheets

TIME STRETCHING BY AVERAGING

TIME STRETCHING BY REPLICATION

TIME STRETCHING BY FRACTIONAL REPRESENTATION

DYNAMIC CORONARY ROADMAPPING

TECHNICAL FIELD

The present invention relates generally to enhancement of X-ray fluoroscopy images and, more particularly to a method of producing a dynamic digital coronary roadmap display overlaid on a fluoroscopic image of a beating heart.

BACKGROUND OF THE INVENTION

This invention concerns an improved method for visualizing a coronary arterial tree known as a roadmap. Such a roadmap is useful during coronary angioplasty operations. In coronary angioplasty a steerable guidewire is guided into specific arterial branches of the heart. A dilation balloon is then directed along the guidewire, placed in position relative to the stenotic or abnormally narrow segment of the artery and then expanded to dilate the artery. Coronary angioplasty is used as an alternative to coronary artery bypass surgery for improving blood flow in patients with coronary artersclerosis.

Steerable guidewires have greatly expanded the use of angioplasty, but correct positioning of the guidewire is hampered by inadequate means to simultaneously visualize the coronary arteries. The methods developed to date largely focus on displaying a static display of the coronary arterial tree taken after injection of a visible contrast medium, over a live fluoroscopic image of the beating heart. Since the contrasting image is static and the live image is dynamic, this overlay method results in substantial misregistration discrepancies. In other words, the static roadmap representation is out of phase with the beating heart during most of the cardiac cycle. This renders accurate visualization difficult.

U.S. Pat. No. 4,204,225, assigned to the Wisconsin Alumni Research Foundation, discloses a method of producing television difference images from an X-ray image of an anatomical subject. The object of this invention is to show circulating blood with enhanced visibility while substantially eliminating bone and soft tissue from the images through subtraction.

The method disclosed includes integrating a mask or initial X-ray image over a predetermined number of television fields before an injected X-ray contrast medium becomes visible. This integrated mask image is then subtracted in real time from later incoming television fields taken after the contrast medium is visible, ultimately producing difference video images. These difference video images represent changes in the X-ray images subsequent to taking of the mask.

Because this method utilizes an integrated mask, it does not take into consideration the motion of the beating heart and accordingly, considerable misregistration errors still exist.

U.S. Pat. No. 4,204,226 assigned to the Wisconsin Alumni Research Foundation is very similar to U.S. Pat. No. 4,204,225. This patent includes creation of a series of television difference images which represent changes in the X-ray image between successive time intervals.

Neither of the above two patents include the step of ECG synchronization to correlate the live and mask images. Generally, cardiologists and radiologists are used to seeing live X-ray images, and viewing live real time subtracted images is distracting and not generally helpful clinically. As a result, the techniques of the above two patents have largely been clinically abandoned.

European patent No. 0,193,712 to Siemmens discloses an X-ray diagnostic device for subtraction angiography. This invention also utilizes a single mask frame and integrates it over a full cycle. By integrating the mask over the full cardiac cycle, the misregistration error is simply distributed and not minimized.

A need therefore exists for a method to produce a representation of the coronary arterial tree which when added to the live fluoroscopic images follows the movement of the heart with a minimum of misregistration. Use of this method would better assist angiographers in accurate placement of guidewires and dilation balloons during coronary angioplasty operations.

SUMMARY OF THE INVENTION

Accordingly, it is a primary object of the present invention to provide a dynamic coronary artery roadmapping procedure overcoming the above-described limitations and disadvantages of the prior art.

Another object of the present invention is to provide a method of enhancing live fluoroscopic images by adding a representation of the coronary arterial tree which persists after disappearance of the contrast dye.

An additional object of the present invention is to provide a method of producing live fluoroscopic images of a beating heart overlaid with a dynamic image of the coronary arterial tree for facilitating guidewire placement, reducing the amount of contrast dye needed and allowing optimal placement of a dilatation balloon during angioplasty.

Still another object of the present invention is to provide a device which produces a dynamic visual roadmap of a coronary arterial tree to better assist angiographers in coronary angioplasty operations.

Yet another object of the present invention is to provide a dynamic visual roadmap of the coronary arterial tree which is added to and moves in substantially precise synchronous motion with the incoming fluoroscopic images of the patient's beating heart.

Additional objects, advantages and novel features of the invention will be set forth in part in the description which follows, and in part, will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as described herein, a method is provided to receive and store incoming X-ray images of the patient's beating heart, thereby creating a mask sequence. Specifically, an X-ray source passes X-rays through the patient striking an image intensifier. A high resolution TV camera receives the image from the image intensifier. The output of the TV camera is passed through a line rate converter. This converter converts the 1024 line image output from the high resolution TV camera to a 512 line image. A video input/output controller receives the 512 line image from the line rate converter and passes it to an image memory where the image is stored. The images thus obtained are stored in the image memory sequentially, frame by frame. This produces an image sequence which when replayed gives the illusion of motion. The sequence length is equal to one full cardiac cycle. One full cardiac cycle by definition exists between receipt of the patient's R-wave and receipt of the next.

After creation of the mask sequence, a visible contrast medium is injected into the patient. A series of X-ray images are again received and stored as described above, thereby creating a contrast sequence.

The contrast sequence is typically longer in duration than the mask sequence due to the physiologic observation that the patient's heart rate slows upon injection of the contrast medium. Accordingly, a method is provided to match the differing sequence lengths. Specifically, the duration of the shorter image sequence is stretched to match that of the longer. This is accomplished by adding filler frames to the shorter sequence thereby matching its length to the longer one. These filler frames can be created by simply replicating the previous frame or by an averaging method which mathematically averages the preceeding and subsequent frames. Another method is to construct a new longer sequence by using fractional frame computations. By this method a weighted frame average is computed based on the extent of temporal overlap between the shorter and longer sequence. Choice of Which method to utilize will depend on which will give the least misregistration for the image sequence itself.

After the image sequences are matched in duration, the contrast sequence is subtracted from the mask by a gated subtraction method. By this method, each frame of the contrast sequence is subtracted from the corresponding frame of the mask sequence. This produces an image of the coronary arterial tree devoid of surrounding tissue and organs. By subtracting the contrast sequence from the mask sequence, the arteries appear light on a dark background.

During angioplasty operations, the roadmap sequence is added to the live video signal of the patient's beating heart. This results in the creation of a roadmap image of the coronary arterial tree. This roadmap moves in precise synchronization with the image of the patient's beating heart. The degree of transparency of the roadmap image is adjustable by the operator.

The replay of roadmap sequence is triggered by receipt of an incoming ECG R-wave. Accordingly, if the live image cardiac cycle is shorter than the roadmap sequence, the sequence automatically resets upon receipt of the next incoming R-wave. If the patient's cardiac cycle is longer in duration than the roadmap sequence, the last frame of the roadmap is reused as needed. This takes advantage of the physiologic observation that bradycardia, or an abnormally slow heart rate, is associated with prolongation of the diastole (the end of the cardiac cycle), with little alteration in systole. Upon a total loss of the ECG R-wave trigger, the last frame of the roadmap sequence is again reused, reverting to a static roadmap mode.

BRIEF DESCRIPTION OF THE DRAWINGS

The accompanying drawing incorporated in and forming a part of the specification, illustrates several aspects of the present invention and together with the description serves to explain the principals of the invention. In the drawing.

Reference will be now made in detail to the present preferred method of the invention, an example of which is illustrated in the accompanying drawing.

DETAILED DESCRIPTION OF THE INVENTION

Figure 1:
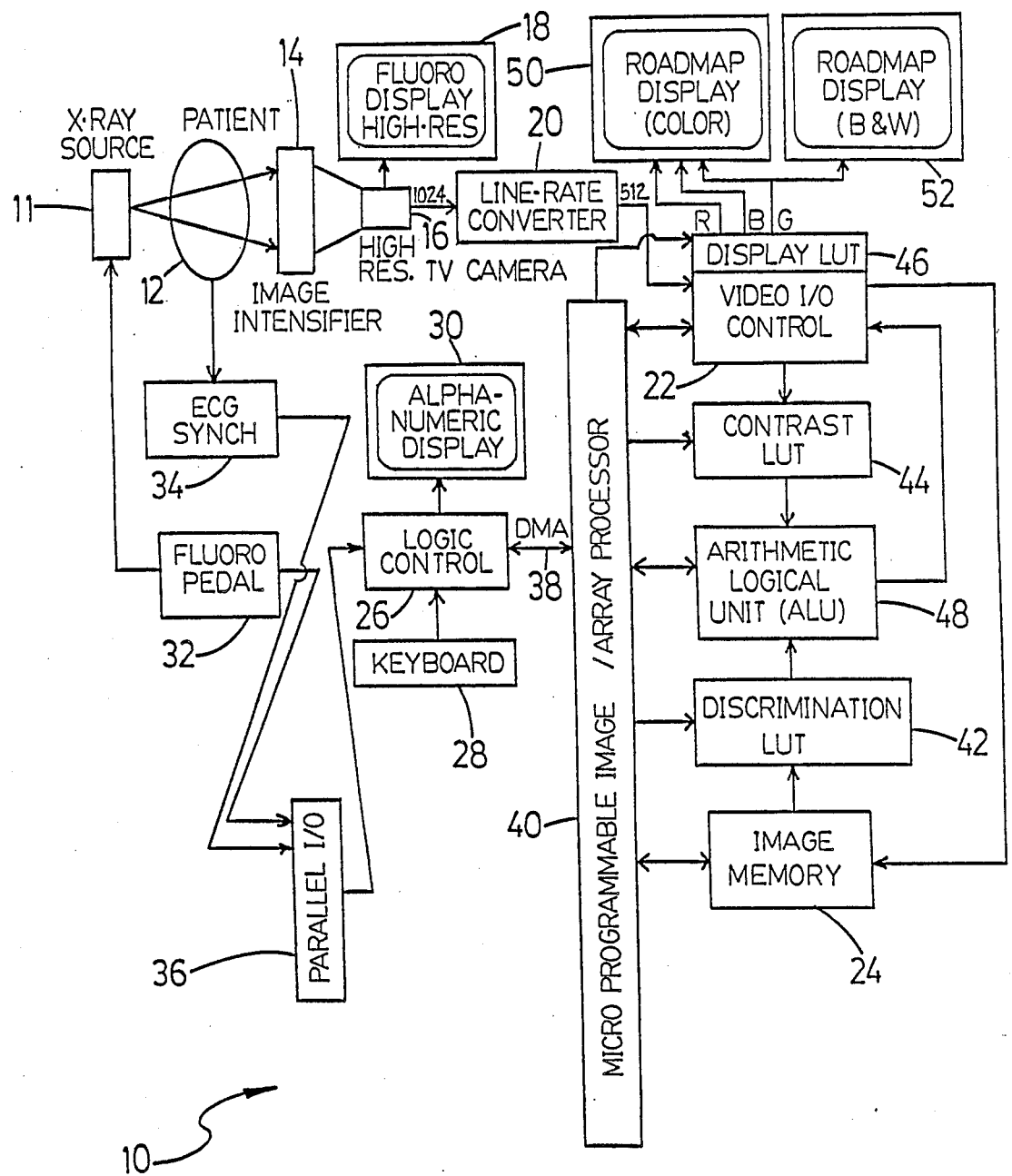
FIG. 1 is a schematic diagram of the hardware of a preferred embodiment of the present invention.

The coronary roadmapping system 10 of the present invention includes an X-ray source 11 as shown in FIG. 1. The X-rays from the X-ray source 11 pass through the patient 12, and strike an image intensifier 14, where they are converted into light. The image on the image intensifier is scanned by a high resolution 1024 line TV camera 16. The output of the camera 16 is displayed on a fluoro display 18 and directed to a line rate converter 20, available, for example, from Krontron Electronics, Mountain View, Calif.

The output of the line rate converter 20 is fed into the video input/output control 22, where it is passed through analog to digital converters and the resulting digital representation of the images in stored in the image memory 24.

The acquisition of images through the system 10 is controlled by a human operator. The system 10 image acquisition is governed by a logic control center 26. The operator communicates with the logic control center 26 via a keyboard 28.

An alphanumeric display 30 of text information is provided to assist the keyboard operator. The X-ray source 11 is activated by the fluoro pedal 32. The information concerning the status of this fluoro pedal 32 is sent to the logic control center 26 through a parallel input/output module 36. An ECG synchronization module is provided to process information concerning receipt of the patient's ECG R-waves. The logic control center 26 passes the above information through a direct memory access channel 38 to the microprogrammable image/array processor (MIAP) 40. An example of an MIAP is "Mipron" available from Krontron Electronics, Mountain View, Calif.

In operation, a mask sequence is created by passing X-rays through the patient as described above. The resulting X-ray mask sequence video is stored in the image memory 24. By utilizing the ECG synchronization module 34, the acquisition of the mask sequence is limited to one full cardiac cycle as, for example, from one R-wave signal to the next.

A visible contrast medium is now injected into the coronary arteries of the patient. X-ray images are once again taken of the patient. The resulting contrast sequences are taken and stored until the image memory 24 is filled.

During contrast sequence acquisition, the MIAP 40 records the contrast sequence frame numbers which correspond to reception of the R-wave as received from the ECG synchronization module 34. The contrast sequence is then analyzed by the MIAP 40 to determine the optimum image contrast. This is done by analyzing the total brightness of the central two-thirds of each image. The greater the radiographic contrast which is present, the lower the total image brightness will be. The optimum contrast sequence is defined as that sequence of frames with the lowest total brightness in the central two-thirds of the images, before any rise in brightness occurs.

Figure 2:
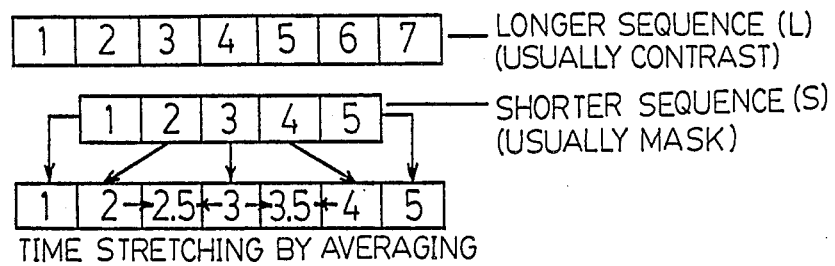
FIG. 2 is a diagram of the various time stretching methods, used in the present invention.
Figure 2:
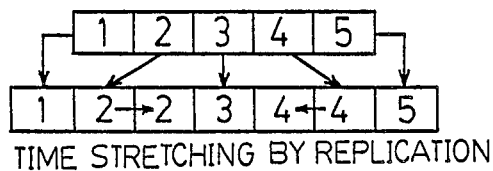
Figure 2:
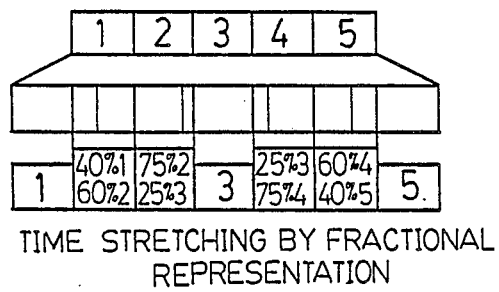

To produce the roadmap sequence, the MIAP 40 first performs a frame by frame gated digital subtraction between the mask sequence and contrast sequences. If the mask and contrast sequence are of different duration, a time stretching method is utilized to elongate the shorter image sequence as shown in FIG. 2. This time stretching method is accomplished in three different ways.

Reference is now made to FIG. 2 showing the methods of performing time stretching. In FIG. 2 a longer sequence (L) and shorter sequence (S) are shown. The technique of time stretching involves adding a number of filler frames (2.5, 3.5) to the shorter sequence (S) to equal the length of the longer sequence (L).

Three methods are provided to create the filler frames. In the first, the filler frames are created by mathematically averaging the preceeding and subsequent frames. In FIG. 2 (upper diagram), the filler frames obtained by the averaging method are shown as an average of frames 2 and 3 and of frames 3 and 4. As a result, the shorter sequence is stretched to match the longer by the addition of frames 2.5 and 3.5.

By the replication method also shown in FIG. 2 (middle diagram), the filler frames are created by simply duplicating the preceeding frame in the sequence. In FIG. 2 the shorter sequence is stretched to match the longer by adding an additional frame 2 and frame 4.

The fractional representation method is the more complicated of the three (see lower diagram). By this method, each frame of the shorter sequence contributes a fractional portion to one or more frames in the longer sequence. As shown, the 5 frames in the shorter sequence have been temporally lengthened to match the duration of the longer 7 frame sequence. Then, the extent of overlap between each frame in the longer sequence and the corresponding frame in the shorter sequence is computed. Finally, new frames are created to reflect the above computed overlap.

The fractional representation method above generally produces a smoother moving image, but depending on the nature of the image sequence, the other methods may produce less misregistration error. This is because small registration errors may be distributed over many frames when the fractional representation method is used.

After the sequence lengths have been equalized, a gated subtraction method is used to create the roadmap image. This is done by subtracting each frame of the contrast sequence from the corresponding mask sequence frame. The result is an image of light arteries on a dark background.

Another important aspect of this invention is found in employing the method of binary discrimination. By utilizing this binary discrimination method, the roadmap image which appears in shades of gray is converted into a substantially pure black and white roadmap image. The method of binary discrimination first includes a computation of a discrimination level. The initial discrimination level is determined by the MIAP 40 by analyzing the distribution of pixel values in the image. The initial discrimination level is selected so that 10% of the pixels in the first frame of the subtracted sequence are brighter than the discrimination level, while the rest are darker.

The operator can change the computed discrimination level in an attempt to better visualize smaller distal vessels. However, a tradeoff exists between visualizing these smaller vessels and the appearance of misregistration artifacts. Generally, the preset discrimination level is adequate.

A discrimination look-up table 42 is provided to set the pixel values below the discrimination level to zero (black) while those above the discrimination level are set to 128.

A contrast look-up table 44 is provided to scale the pixels of incoming images having input values of 0–255 down to the range of 0–127. The brightness of the final images can be adjusted by the operator by adjusting the center of the input range. The contrast can be adjusted by altering the width of the imput range.

To create the dynamic roadmap display, incoming video images are transformed through the contrast LUT 44 and combined with the roadmap sequence which is held in the image memory of the system. Replay of the roadmap sequence is triggered by timing information received from the ECG synchronization module 34. Due to the manner in which the contrast LUT and discrimination LUT values are assigned, the addition produces pixels in the range of 0–127 for portions of the image which were not contained within the coronary arteries of the original injections and in the range of 128–255 for those that were contained within the coronary artery. Each frame of the fluoroscope image is added to each frame of the roadmap sequence. This addition occurs sequentially frame by frame throughout the entire cardiac cycle.

The color and transparency of the final mixed images is controlled by the display LUT 46. The values in this LUT are computed such that the pixels with values 0–127 are displayed as black and white pixels while those in the range of 128–255 are displayed similarly, but with the addition of a light green tint. The images can now be displayed either on the color roadmap display 50 or the black and white roadmap display 52.

When an R-wave is detected by the ECG synchronization module, the roadmap image is reset to the beginning, allowing proper tracking of rapid heart rates. If, on the other hand, the end of the roadmap sequence is reached without detection of an R-wave, the last frame of the roadmap is reused as needed. This takes advantage of the physiologic observation that bradycardia is associated with prolongation of the end of the heart beat (diastole) with little alteration of the beginning of the heart beat (systole). Upon total loss of an ECG signal, the last frame of the roadmap sequence is continually reused reverting to a static rather than a dynamic roadmap mode.

In summary, numerous benefits result from employing the concepts of the present invention. The method herein disclosed reveals a method of displaying a representation of the dynamically beating coronary arterial tree in combination with live incoming fluoroscopic images using ECG synchronization. The resulting dynamic roadmap display is of tremendous benefit to angiographers, in that it holds considerable promise for facilitating guidewire placement and assisting with optimal placement of the dilatation balloon.

The foregoing description of a preferred embodiment of the invention has been presented for purposes of the illustration and description. It is not intended to be exhaustive or to limit the invention to the precise method disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications. All such modifications and variations are within the scope of this invention as determined by the appended claims when interpreted with breadth to which they are fairly, legally and equitably entitled.

I claim:

1. Method for producing a dynamic coronary artery system roadmap of a patient comprising the steps of:
   recording and storing a dynamic visual image of a beating heart for a cardiac cycle so as to create a mask sequence;
   injecting a visual contrast medium into the coronary artery system of the patient;
   recording and storing a corresponding dynamic visual image of the beating heart for another cardiac cycle after injecting the contrast medium so as to create a contrast sequence; and
   subtracting the corresponding contrast sequence from the mask sequence in order to produce the roadmap sequence of the coronary artery system.

2. The method of claim 1 wherein said subtracting step is performed in accordance with a gated subtraction process including the step of synchronizing the beginning of the mask and contrast sequences.

3. The method of claim 2 wherein the gated subtraction process includes a further step of frame by frame matching of the contrast and mask sequences.

4. The method of claim 3 wherein the gated subtraction process includes a further step of time stretching for matching the mask sequence to the contrast sequence where the mask and contrast sequences are of different duration.

5. The method of claim 4 wherein the time stretching is accomplished by adding filler frames to whichever sequence is shorter in duration, said filler frames being distributed evenly throughout the shorter duration sequence by replicating the preceding frame in the sequence.

6. The method of claim 4 wherein the time stretching is accomplished by adding filler frames to whichever sequence is shorter in duration, said filler frames being created by computing an average of the preceding and subsequent frame in the sequence between which a filler frame is to be positioned.

7. The method of claim 4 wherein the time stretching is accomplished by creating an entirely new sequence wherein each frame in the sequence of shorter duration contributes a fractional portion to one or more frames in the new sequence.

8. Method for producing a dynamic coronary artery system roadmap of a patient comprising the steps of:
   recording and storing a dynamic visual image of a beating heart for a substantially full cardiac cycle so as to create a mask sequence;
   injecting a visual contrast medium into the coronary artery system of the patient;
   recording and storing another dynamic visual image of the beating heart for a substantially full cardiac cycle after injecting the contrast medium so as to create a contrast sequence; and
   producing a substantially full contrast roadmap sequence.

9. The method of claim 8 wherein the producing step is performed in accordance with a binary discrimination process including the steps of computing the discrimination value for image brightness, and assigning all areas in the picture brighter than the determined value to white and all areas darker than the determined value to black thereby creating a substantially full contrast black and white image without shades of gray.

10. A method of displaying a representation of a dynamically beating coronary arterial system to assist in coronary angioplasty, comprising the steps of:
    recording and storing dynamic visual images of a beating heart thereby creating a mask sequence of a complete cardiac cycle;
    injecting a visual contrast medium into the patient;
    recording and storing dynamic visual images of the beating heart after injecting the contrast medium thereby creating a contrast sequence of a complete cardiac cycle;
    subtracting the contrast sequence from the mask sequence so as to create a preliminary roadmap sequence;
    producing a substantially full contrast roadmap sequence from the preliminary roadmap sequence;
    adding the full contrast roadmap sequence to a live dynamic visual image of the beating heart to produce an image of the roadmap overlaid on the image of the heart that moves in substantial synchronization with the beating heart thereby allowing an angiographer to accurately visualize the placement of a dilation balloon throughout the complete cardiac cycle.

11. The method of claim 10, wherein the method includes the step of triggering replay of the roadmap sequence in response to an incoming ECG R-wave signal so as to substantially synchronize the roadmap sequence with the actual beating of the heart at faster rates.

12. The method of claim 11 including the step of reusing a final frame of roadmap sequence frame until reception of the next incoming ECG R-wave so as to substantially synchronize the roadmap sequence with the actual beating of the heart at slower rates.

13. Apparatus for producing a dynamic coronary artery system roadmap of a patient including:
    means for recording and storing a dynamic visual image of a beating heart for a cardiac cycle so as to create a mask sequence;
    means for recording and storing a corresponding dynamic visual image of the beating heart for another cardiac cycle after injecting a contrast medium so as to create a contrast sequence;
    means for matching sequences of different length by time stretching;
    means for subtracting said corresponding contrast sequence from said mask sequence producing the roadmap sequence; and
    means for producing a substantially full contrast sequence by binary discrimination.

* * * * *